United States Patent [19]

Mintz

[11] Patent Number: 4,847,084
[45] Date of Patent: Jul. 11, 1989

[54] OINTMENT FOR THE TREATMENT OF DECUBITI ULCERS

[76] Inventor: Morris Y. Mintz, 262 Woodcrest Rd., Paramus, N.J. 07652

[21] Appl. No.: 83,360

[22] Filed: Aug. 10, 1987

[51] Int. Cl.$^4$ .................. A61K 31/40; A61K 31/165; A61K 33/18; A61K 37/547
[52] U.S. Cl. .................................. 424/94.2; 424/94.61; 424/94.64; 424/195.1; 424/80; 514/410; 514/628; 514/928
[58] Field of Search ................. 424/94.2, 94.61, 94.64, 424/150, 195.1; 514/928, 628, 410

[56] References Cited

U.S. PATENT DOCUMENTS 4,645,668  2/1987  Pinnell ................................ 424/94.2
4,678,668  7/1987  Darras ................................ 424/94.2

OTHER PUBLICATIONS

Professional Guide to Drugs, Second Ed., 1982, pp. 964-966, 850-851.
American Drug Index, 1980, pp. 135, 137.

*Primary Examiner*—Johnnie R. Brown
*Assistant Examiner*—Jacqueline M. Stone

[57] ABSTRACT

These 2 formulae provide a new and unique method of healing decubiti ulcers. Formula #1 contains Fibrinolysin and Desoxyribonuclease, Combined-Bovine-with Chloramphenicol Ointment, Chlorophyll Ointment 0.5%, and Povidone-Iodine Ointment 10% in equal parts of each. Formula #2 contains Fibrinolysin and Desoxyribonuclease, Combined-Bovine-Ointment, Chlorophyll Ointment 0.5%, and Povidone-Iodine Ointment 10% in equal parts of each. This new unique method of healing decubiti ulcers depends on a combination of actions which include enzymatic debriding properties, infection control, wound odor control, and promotes granulation that produces a clean base for total healing of the ulcer in a much shorter time than any formulae for this purpose heretofore.

2 Claims, No Drawings

OINTMENT FOR THE TREATMENT OF DECUBITI ULCERS

My product is called Decubicare Ointment.

There are at present several products available for the treatment of decubiti ulcers, for example: Elase Ointment, Elase Chloromycetin Ointment, Panafil Ointment, Granulex Aerosol, Travase Ointment, and Santyl Ointment.

Elase Ointment contains 2 lytic enzymes (Fibrinolysin and Desoxyribonuclease in an ointment base). Elase-Chloromycetin Ointment contains these same 2 lytic enzymes plus an antibiotic (Chloramphenicol) in an ointment base. Both are manufactured by Parke-Davis, 201 Tabor Road, Morris Plains, N.J. 07950.

Panafil Ointment is an enzymatic debriding-healing ointment which contains Papain, Urea U.S.P., and water soluble Chlorophyll derivatives in a hydrophilic ointment base, and is manufactured by Rystan Company Inc., P.O. Box 214, Little Falls, N.J. 07424.

Granulex Aerosol contains Trypsin, Balsam Peru, Castor Oil, and an emulsifier and is applied as an aerosol spray. It is manufactured by Dow B. Hickam, Inc., P.O. Box 2006, Sugar Land, Tex. 77487.

Travase Ointment is a sterile preparation of proteolytic enzymes, elaborated by Bacillus subtilis in a hydrophilic ointment base and is manufactured by Flint, one Baxter Pkwy, Deerfield, Ill. 60015. Santyl Ointment is an enzymatic debriding ointment containing Collagenase, which is derived from the fermentation by Clostridium histolyticum, and is incorporated into an ointment base. It is manufactured by Knoll Pharmaceuticals, Whippany, N.J. 07981.

All these products have, in my opinion, failed to live up to their claims of healing decubiti ulcers satisfactorily and have been disappointing in many instances.

My product is a new product combining the properties of several of these listed and the combination gives it its unique healing properties not seen with the other products mentioned. The basis of my product's action depends on enzymatic debriding properties, infection control, wound odor control, and promotes wound granulation that produces a clean base for total healing of the ulcer in a much shorter time than any formulae for this purpose heretofore.

I have developed 2 formulations for the treatment of decubiti ulcers entitled: Decubicare Ointment (formula #1 and formula #2).

Formula #1:
  Fibrinolysin and Desoxyribonuclease, Combined-Bovine-with Chloramphenicol Ointment
  Chlorophyll Ointment 0.5%
  Povidone-Iodine Ointment 10%
  Take equal parts of each and make an ointment.
  Apply as directed.

Formula #2:
  Fibrinolysin and Desoxyribonuclease, Combined-Bovine-Ointment
  Chlorophyll Ointment 0.5%
  Povidone-Iodine Ointment 10%
  Take equal parts of each and make an ointment.
  Apply as directed.

Formula #1 would be used when the antibiotic action of Chloramphenicol is needed.

Formula #2 would be used when the antibiotic action of Chloramphenicol is *not* needed.

I claim:

1. A composition for the treatment of decubiti ulcers consisting of equal parts each of the following ingredients:
  Fibrinolysin and Desoxyribonuclease, Combined-Bovine-with Chloramphenicol Ointment;
  Chlorophyll Ointment 0.5%;
  Povidone-Iodine Ointment 10%.

2. A composition for the treatment of decubiti ulcers consisting of equal parts each of the following ingredients:
  Fibrinolysin and Desoxyribonuclease, Combined-Bovine- Ointment;
  Chlorophyll Ointment 0.5%;
  Povidone-Iodine Ointment 10%.

* * * * *